(12) United States Patent
Münch

(10) Patent No.: US 6,717,675 B1
(45) Date of Patent: Apr. 6, 2004

(54) SYSTEM AND METHOD FOR DETERMINING FIBER ORIENTATION IN FIBROUS MATERIAL WEBS

(75) Inventor: Rudolf Münch, Königsbronn (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/534,331

(22) Filed: Mar. 24, 2000

(30) Foreign Application Priority Data

Mar. 26, 1999 (DE) .......................... 199 13 924

(51) Int. Cl.$^7$ .............................................. G01N 21/84
(52) U.S. Cl. .................... 356/429; 250/559.09
(58) Field of Search ................. 356/429, 430, 356/369; 250/559.01, 559.03, 559.09, 559.08

(56) References Cited

U.S. PATENT DOCUMENTS

| | | | | |
|---|---|---|---|---|
| 4,028,728 A | * | 6/1977 | Sharp .......................... | 348/131 |
| 4,648,712 A | | 3/1987 | Brenholdt | |
| 5,237,181 A | * | 8/1993 | Kerkhoff et al. ....... | 250/559.08 |
| 5,475,233 A | * | 12/1995 | Fukuoka et al. .......... | 250/559.1 |
| 5,598,266 A | * | 1/1997 | Cornuejols ................. | 356/367 |
| 5,666,199 A | * | 9/1997 | Hess et al. .................. | 356/364 |

FOREIGN PATENT DOCUMENTS

| | | |
|---|---|---|
| DE | 2214191 | 12/1972 |
| DE | 2900928 | 7/1979 |
| DE | 3603235 | 8/1986 |
| GB | 2015155 | 9/1979 |

OTHER PUBLICATIONS

Report of Sulzer–Escher Wyss GmbH, Ravensburg, No. Jun. 1, 1989, Münch et al..
Report No. Apr. 6, 1984, Weisshuhn.
Article by Weisshuhn et al., entitled "Einfluss des Stoffauflaufs auf die Blatteigenschaften und deren Konstanz" ["Influence of the Flow of Material on the Sheet Characteristics and their Consistency"] in a special edition of the journal *Das Papier*, No. 10, vol. 40.

Article "High–Resolution Fibre Orientation and Basis Weight Measurement" by B. Druin et al. in the *Journal of Pulp and Paper Science*, vol. 22, No. 7, Jul. 7, 1996.

\* cited by examiner

Primary Examiner—Zandra V. Smith
(74) Attorney, Agent, or Firm—Greenblum & Bernstein, P.L.C.

(57) ABSTRACT

A system and method for determining the orientation of fibers in a fibrous material web. The system includes at least one source of electromagnetic radiation disposed on one side of the fibrous material web, at least one sensor for sensing the electromagnetic radiation emitted by the at least one source disposed on another side of the fibrous material web, and at least one optical device disposed between the at least one source and the at least one sensor, wherein the electromagnetic radiation travels through the at least one optical device and the fibrous material web such that the at least one optical device influences a propagation of the electromagnetic radiation as a function of its polarization properties. The method includes exposing a first side of the fibrous material web to electromagnetic radiation from at least one source, allowing the electromagnetic radiation to penetrate to a second side of the fibrous material web, influencing a propagation of the electromagnetic radiation as a function of its polarization properties with at least one optical device disposed between the at least one source and at least one sensor, and sensing the electromagnetic radiation on the second side with the at least one sensor.

55 Claims, 4 Drawing Sheets

A-A

B-B

A-A

B-B

A-A

SYSTEM AND METHOD FOR DETERMINING FIBER ORIENTATION IN FIBROUS MATERIAL WEBS

CROSS-REFERENCE TO RELATED APPLICATIONS

The present application claims priority under 35 U.S.C. §119 of German Patent Application No. 199 13 924.5, filed on Mar. 26, 1999, the disclosure of which is expressly incorporated by reference herein in its entirety.

BACKGROUND OF THE INVENTION

1. Field of the Invention

The invention relates to a system and a method for determining the orientation of fibers in fibrous material webs, particularly paper webs.

2. Discussion of Background Information

The article "High-Resolution Fibre Orientation and Basis Weight Measurement" by B. Drouin et al. in the *Journal of Pulp and Paper Science*, Vol. 22, No. 7, Jul. 7, 1996 mentions an instrument with which the fiber orientation in paper is measured by a transmission measurement with a rotating plane of polarization. The instrument is based on filtered black body radiation in the far infrared region (FIR) of the electromagnetic spectrum. Some disadvantages of this conventional device are its high cost and the fact that it works with only one wavelength.

SUMMARY OF THE INVENTION

The invention provides for a system and a method of the type initially described, in which the fiber orientation can be determined more efficiently and with high precision.

The invention utilizes at least one source of electromagnetic radiation disposed on one side of a fibrous material web and at least one sensor for receiving the radiation emitted by the source disposed on the other side. The radiation from the source penetrates the fibrous material from one side and is sensed on the other side. Moreover, at least one optical device, for influencing the propagation of the radiation as a function of its polarization properties, can be positioned in the path of the radiation, e.g., between the source and the sensor.

It has been discovered that the interaction between electromagnetic radiation and fibrous material webs having a homogeneous or at least dominant or prevalent fiber orientation, can be used to obtain information from which the fiber orientation can be determined. In principle, any desired wavelengths of the radiation can be used. However, wavelengths in the realm of visible light and/or infrared radiation are preferred. Moreover, NIR (Near Infrared Radiation) is most preferred. Additionally, other wavelengths may be utilized or required at the same time so that the system can cope with the differing ash content and/or other variations of the paper properties.

The optical system of the invention utilizes radiation whose propagation has been influenced to produce linearly polarized radiation. The invention may use completely unpolarized radiation from various sources, such as a natural light source, partially unpolarized light, or unpolarized radiation. This radiation which is emitted from the source can then be linearly polarized prior to entering and/or interaction with the fibrous material web. In this case, the optical system then serves as a polarizer. Alternatively, the radiation which is emitted from the source can then be linearly polarized after passing through and/or interaction with the fibrous material web. In this case, the optical system is used as an analyzer. Such a design allows the direction of polarization of linearly polarized radiation to be detected after the radiation has passed through the fibrous material web.

The invention takes advantage of the fact that the propagation of linearly polarized radiation is influenced to the extent that the intensity of the linearly polarized radiation, that the optical device permits to pass, is a function of its direction of polarization.

In at least one embodiment of the invention, the optical system includes at least one polarizing filter. With filters of this type, it is possible both to produce linearly polarized radiation and to determine the polarization direction of linearly polarized radiation. Moreover, the use of such a polarizing filter permits the implementation of many different arrangements, all of which are characterized by comparatively simple construction in terms of measurement technology as well as a high degree of measuring precision.

Thus, it is possible to arrange a system having a single optical device in the form of a polarizing filter located between the source and the fibrous material web. The invention provides for the intensity of the linearly polarized radiation, which is produced by the polarizing filter and penetrates the fibrous material web, to be measured by sensor changes as a function of the orientation of the polarizing filter relative to the orientation of the fibers in the fibrous material web. Utilizing this technique, the fiber orientation can be determined in a comparatively simple manner by utilizing repeated measurements of intensity at different orientations of the polarizing filter relative to the fibrous material web. Such a system design can utilize a polarizing filter which is mounted such that it can rotate about an axis running perpendicular to the fibrous material web running direction.

The system functions as follows: It is assumed that a measured light intensity depends on the main fiber orientation in the paper and on the orientation of the polarization filters. The measured light intensity will be highest if the polarization filter and the fibers are oriented in the same direction (at 0° and 180°). The measured light intensity will be lowest in the orthogonal directions (at 90° and 270°). It is further assumed that the intensity distribution in polar coordinates has therefore about an elliptical shape: the largest diameter at 0° (a), and the smallest diameter at 180° (b).

If the difference a–b is high, the fibers are very strongly oriented only in one direction. However, if the difference is small, there is only a very small orientation or an almost equal distribution of the fibers.

Accordingly, if the highest signal is attained, when the orientation of the polarization filter corresponds exactly to machine direction of the paper, the fiber orientation is 0° relative to the machine direction. Otherwise, the fibers are not oriented properly in the machine direction. Acceptable or desired values are between approximately –2° and approximately +2°, while unacceptable or undesired values are larger than approximately 10°.

Thus, an algorithm may be utilized which has two parts: the data of the ellipse, and the relationship or how this data relates to paper properties. Accordingly, in order to calculate the orientation/shape of the ellipse, at least (3) three measurements have to be taken (three signals with polarizing filters in three different orientations). This can be performed using the usual quadratic equations which use the known properties of the ellipses.

In order to relate these data to the paper properties, empirical solutions are required. The signals a and b (and/or algorithmical combinations of these signals like a–b, a+b, and a/b), and the orientation angle of the ellipses are compared to lab tests. Thus, one can use e.g., Least Squares methods like "Partial Least Squares" (or other similar methods) in order to derive formulas to derive paper properties from the characteristics of the ellipse.

On the other hand, breaking load ellipses are something similar. Sample paper strips are typically taken having three different angles relative to the machine direction (i.e., –30°, 30°, and 0°). From these three measurement values, an ellipse is calculated. Accordingly, the ellipse reflects the strength properties of the paper. The strength is greatest in the direction of the main fiber orientation and lowest in a direction orthogonal to it. Thus, the strength properties in different angles serve as an indication of the fiber orientation. Unfortunately, this technique cannot be performed on line as it requires that the paper samples or sections be removed or cut from the web.

Accordingly, the system may utilize several fixed polarizing filters which have defined orientations or polarization directions when in the measurement position instead of one or more movable polarizing filters. This design allows the filters to be exchanged quickly. Moreover, the filters may be arranged in a configuration known as a filter wheel.

According to another variant of the invention, a single polarizing filter is positioned between the fibrous material web and the sensor with the source being located on the other side of the fibrous material web. This design or arrangement exploits the capability of a fibrous material web having an at least dominant or prevalent fiber orientation to linearly polarize incident radiation, at least to a small degree, by interacting with the incident radiation. The polarization direction dependent on the fiber orientation can be detected with the polarizing filter, which serves as an analyzer in this arrangement. In this arrangement, the fiber orientation can be detected by measuring the intensity of the radiation which is permitted to pass through the polarizing filter as a function of the orientation of the polarizing filter relative to the fibrous material web.

In yet another variant of the invention, at least one polarizing filter is utilized on each side the fibrous material web. In this arrangement, one polarizing filter located between the source and the web. This filter produces linearly polarized radiation from source radiation. Another filter is located between the web and a sensor device. This filter is used to detect the direction of polarization. In this arrangement, either of the two polarizing filters or both can be mounted such that they can rotate about an axis running perpendicular to a plane defined by the fibrous web running direction.

In another embodiment of the invention, a single polarizing filter is positioned between the source and one side of the fibrous material web. A plurality of polarizing filters are located on the other side of the fibrous material web. This arrangement also utilizes a sensor associated with each of these polarizing filters. Moreover, these filters can have different polarizing orientations relative to the fibrous material web travel direction. Additionally, in this design, because of the different orientations of the polarizing filters on the sensor side, none of the optical devices need be mounted so as to rotated relative to the fibrous material web. This is because two or more measurements can be performed at different relative orientations between the fibrous material web. Such a design allows for the detection of the fiber orientation.

In many of the embodiments, it is preferred that the source side polarizing filter be oriented such that the polarization direction of the linearly polarized radiation produced runs which are parallel to the travel or running direction of the fibrous material web. The sensor side polarizing filters can be either rotatably mounted so that they rotated opposite to one another. Alternatively, these sensor side filters can be non-rotatably mounted and oriented in a symmetrical manner relative to the web travel direction. Thus, for example, two sensor side filters can be provided, each of which has a sensor associated with it, which can rotated in opposite directions, for example, by approximately 30° or 45° relative to the web travel direction. The advantage of this arrangement is that there are minimal moving parts, which thereby avoids wear problems.

In general, it is possible to detect the fiber orientation with radiation of a single wavelength using the invention. However, since the interaction between the fibrous material web and the radiation is a function not only of the fiber orientation itself and additional factors such as the fiber length, fiber type and additional constituents and properties of the fibrous material web, but also of the wavelength of the radiation used for the measurement, more meaningful results can be obtained using several different wavelengths.

The invention also contemplates the use of individual radiation sources, each of which emits radiation at a specific wavelength, to be activated one after the other. In this case, a sensor of comparatively simple design, for example, a photodiode, can be used. This sensor would provide a signal representing the intensity thereof for each incident radiation.

On the other hand, it is preferred that a source which emits a discrete and/or continuous wavelength spectrum be used. This design makes it is possible to work simultaneously with different wavelengths. In this case, a sensor serving as a spectrometer can be used. The sensor is capable of detecting the intensity of the incident radiation separately by wavelength in order thus to be able to evaluate the signals separately by wavelength.

Moreover, the invention also provides that at least one source of electromagnetic radiation is arranged on one side of the fibrous material web. On the other side of the web is disposed at least one sensor for sensing the radiation emitted by the source and penetrating the fibrous material web. A polarizing filter is positioned between the source and the sensor device for influencing the propagation of the radiation as a function of its polarization characteristics. This filter may be located on either side of the web so that it is between the web and the source or between the web and sensor device. Additionally, the filter may be located on both sides of the web.

In this process, the fiber orientation is preferably detected in a moving fibrous material web, particularly a paper web moving at normal speed in a papermaking machine.

Such an on-line measurement of the fiber orientation makes it possible to intervene in the manufacturing process for the fibrous material web immediately after detecting a deviation from the desired fiber orientation and thus to create a rapid control loop.

According to one aspect of the invention, there is provided a system for determining the orientation of fibers in a fibrous material web, the system including at least one source of electromagnetic radiation disposed on one side of the fibrous material web, at least one sensor for sensing the electromagnetic radiation emitted by the at least one source disposed on another side of the fibrous material web, and at least one optical device disposed between the at least one source and the at least one sensor, wherein the electromagnetic radiation travels through the at least one optical device and the fibrous material web such that the at least one optical device influences a propagation of the electromagnetic radiation as a function of its polarization properties. The fibrous material web may be a paper web. The at least one optical device may provide for the transmission of linearly polarized radiation. The at least one optical device may be a polarizing filter. The polarizing filter may be rotatably mounted about an axis. The axis may be approximately perpendicular to a running direction of the fibrous material web. The at least one optical device may include at least two optical devices, one optical device being disposed on one side of the fibrous material web and another optical device being disposed on another side of the fibrous material web. The at least one optical device may comprise at least two optical devices, the at least two optical devices being disposed on one side of the fibrous material web. The at least two optical devices may be disposed between the at least one sensor and the fibrous material web. Each of the at least two optical devices may have a different orientation relative to a running direction of the fibrous material web.

The system may further comprise at least one optical device disposed between the at least one source and the fibrous material web. The at least two optical devices may be oriented symmetrically relative to the at least one optical device. Each of the at least two optical devices may be rotatably mounted about an axis. Each of the at least two optical device may be rotatable in opposite directions from one another. The at least one optical device may comprise a single optical device disposed between the at least one sensor and the fibrous material web. The electromagnetic radiation emitted by the at least one source may be polarized before it passes through the fibrous material web. The single optical device may be rotatably mounted. The at least one optical device may comprise a single optical device disposed between the at least one source and the fibrous material web. The electromagnetic radiation sensed by the at least one sensor may pass through the fibrous material web without being polarized. The single optical device may be rotatably mounted. The at least one sensor may comprise at least two sensors, each of the sensors being associated an optical device. The electromagnetic radiation may comprise one of a discrete and a continuous wavelength spectrum. The electromagnetic radiation may comprise a discrete and a continuous wavelength spectrum. The electromagnetic radiation may comprise one of visible light and infrared radiation. The electromagnetic radiation may comprise visible light and infrared radiation. The at least one sensor may comprise one of a spectrometer and a photodiode. The at least one sensor may be coupled to an analysis unit.

According to another aspect of the invention, there is provided a method for determining the orientation of fibers in a fibrous material web, the method including exposing a first side of the fibrous material web to electromagnetic radiation from at least one source, allowing the electromagnetic radiation to penetrate to a second side of the fibrous material web, influencing a propagation of the electromagnetic radiation as a function of its polarization properties with at least one optical device disposed between the at least one source and at least one sensor, and sensing the electromagnetic radiation on the second side with the at least one sensor. The fibrous material web may be a paper web. The at least optical device may comprise a polarizing filter disposed between the at least one source and the at least one sensor. The influencing may further comprise disposing a first optical device on the first side and a second optical device on the second side. The influencing may further comprise rotating the first optical device about an axis.

The second optical device may comprise a plurality optical devices. The plurality of optical devices may be arranged adjacent one another, each of the plurality being oriented to influence the propagation differently. The influencing may further comprise rotating the second optical device about an axis. The influencing may further comprise continuously moving the fibrous material wed between the first optical device and the second optical device. The influencing may further comprise continuously moving the fibrous material wed between the at least one source and the at least one sensor.

The method may further comprise analyzing a signal generated by the at least one sensor using an analyzer which is coupled to the at least one sensor. The method may further comprise analyzing the electromagnetic radiation after sensing. The analyzing may further comprise analyzing the electromagnetic radiation separately by wavelength. The exposing may comprise using a plurality of different sources. The different sources may vary a wavelength of the electromagnetic radiation over time. The exposing may comprise varying a wavelength of the electromagnetic radiation over time. The method may further comprise analyzing a signal generated by the at least one sensor using an analyzer which is coupled to the at least one sensor to determine one of a difference signal, a summation signal and a ratio signal. The method may further comprise analyzing signals generated by a plurality of sensors using an analyzer which is coupled to the plurality and determining one of a difference signal, a summation signal and a ratio signal. The determining may comprise determining a difference signal, a summation signal and a ratio signal. The method may further comprise moving the fibrous material web between the at least one source and the at least one sensor. The moving may be at a constant speed. The fibrous material web may be a paper web.

The electromagnetic radiation may comprises one of a visible light and a infrared radiation. The influencing may comprise first polarizing the electromagnetic radiation on the first side using a first polarizing filter and second polarizing the electromagnetic radiation on the second side using a second polarizing filter. One of the first polarizing filter and the second polarizing filter may be rotatable. The first polarizing may comprise using a rotatable first polarizing filter. The second polarizing may comprise using a plurality of oriented second polarizing filters. Each of the plurality of second polarizing filters may be rotatable.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1A:
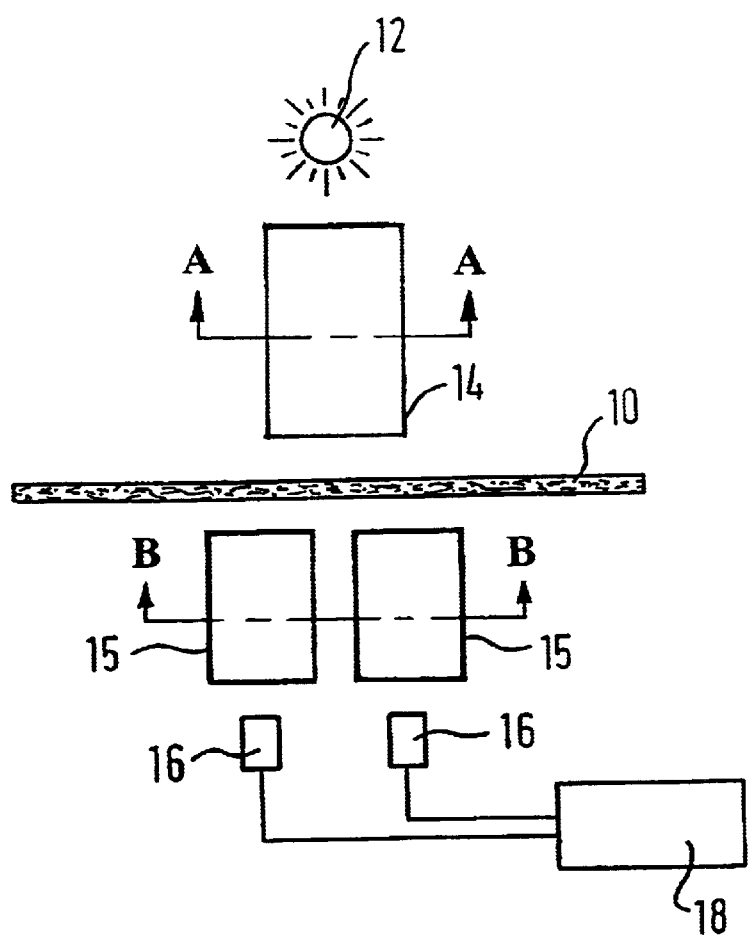
FIG. 1a shows one embodiment of a system for determining fiber orientation which uses a single source side polarizing filter and a plurality of sensor side polarizing filters.
Figure 1B:
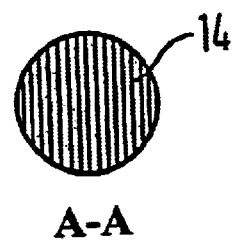
FIG. 1b shows a cross-section A—A view of the source side polarizing filter with polarizing oriented parallel to the web running direction.
Figure 1C:
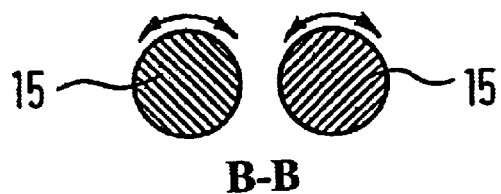
FIG. 1c shows a cross-section B—B view of the sensor side polarizing filters with polarizing symmetrically oriented an angle the web running direction.

FIGS. 1a–c shows an embodiment of a system for determining fiber orientation in a moving paper web 10, whose travel direction is perpendicular to the plane of the drawing. That is, the web is seen from a direction which is transverse to the web running direction so that the web width is clearly seen.

The system according to the invention includes several optical devices, provided in the form of polarizing filters 14, 15. In order to illustrate the measurement principle explained below, the polarizing filters 14, 15 are each shown in FIGS. 1b and 1c, in top or cross-section view.

Arranged between a light source 12 emitting visible light and paper web 10 is a polarizing filter 14, whose direction of polarization is oriented parallel to the travel direction of the paper web 10, i.e., this filter is used to produce linearly polarized light whose direction of polarization is parallel to the web travel direction, as indicated by the hatching in filter 14 (see FIG. 1b).

As an alternative to a visible light source 12, at least one radiation source may also be used, which emits radiation invisible to the human eye. This radiation may be, for example, infrared radiation. Moreover, this aspect applies to all embodiments of the invention described herein.

The light source 12 is preferably designed to emit a wavelength spectrum that either contains multiple discrete wavelengths or is a continuous spectrum. In principle, a superposition of a discrete spectrum and a continuous spectrum is also possible.

On the opposite side of the paper web 10 is arranged two additional polarizing filters 15 which are located next to one another on a plane which runs perpendicular to the web travel direction. Associated with each of these filters 15, is a sensor 16 designed to detect the light which is emitted by the light source 12 and penetrates the paper web 10. Sensors 16 are designed as spectrometers which can measure the intensity of the incident radiation separately by wavelength. The signals provided by sensors 16 are delivered to a common analysis unit 18.

FIG. 1c shows the differences in hatching in the filters 15 arranged between the paper web 10 and the sensors 16. Filters 15 are symmetrically oriented differently such that their directions of polarization are each at an angle of approximately 45° to the travel direction of the paper web 10. Moreover, this angle is also approximately 45° to the direction of polarization of the filter 14 located on the other side of the fibrous material web 10. Filters 15 can also be rotated by other angles relative to the web travel direction, for example, by approximately 30° each, so that the directions of polarization of filters 15 form an angle of approximately 60°. Preferably, the polarizing filters 15 are each oriented symmetrically with respect to the web travel direction and the direction of polarization of the filter 14 associated with the light source 12, as shown in FIGS. 1a–c.

It should be noted that the invention contemplates that more than two polarizing filters can be provided on the sensor side of the paper web 10 (the side facing away from the light source 12). There would of course be a sensor for measuring the intensity of the radiation passing through that filter associated with each filter 15. For example, five (only two are shown) polarizing filters 15 can be arranged in a plane which is transverse to the web travel direction. These filters 15 are irradiated simultaneously by the light or radiation emitted by source 12 after the light or radiation passes through filter 14 and paper web 10. In this embodiment, the orientations of filters 15 relative to paper web 10 or the web travel direction, is chosen such that the directions of polarization form different angles with the web travel direction of, for example, 0°± approximately 15° and ± approximately 30°.

In the variants described above in connection with FIGS. 1a–c, the orientations of polarizing filters 14, 15 are retained (not changed) during measurement. Moreover, the signals supplied by sensors 16 associated with individual filters 15 are placed in relation to one another in order to detect the fiber orientation. The invention also contemplates the use of even more than five filters 15 because the greater the number of polarizing filters 15 used on the sensor side of the web, the more definitive or precise are the measurement results that can be obtained.

By utilizing analysis unit 18, a difference signal, a summation signal, and a ratio signal are formed, generated or produced from the signals supplied by the two or more sensors 16. In this context, the difference signal represents a measure of the fiber orientation relative to the known orientation of polarizing filter 14 associated with light source 12 and thus relative to the travel direction of the paper web 10. While the ratio of the two signals to one another is a measure of the uniform distribution of the orientations of the individual fibers in the paper web 10. The summation signal can be used to normalize the measurements.

In principle, the three aforementioned signals, namely the difference signal, the summation signal, and the ratio signal, suffice to identify what is known as a breaking load ellipse, which serves to identify the fiber orientation and/or distribution. Such breaking load ellipses are described, for example, in the reports of Sulzer-Escher Wyss GmbH, Ravensburg, No. 6/1/89, Münch et al., and No. 4/6/84, Weisshuhn, as well as in an article by Weisshuhn et al. entitled "Einfluβ des Stoffauflaufs auf die Blatteigenschaften und deren Konstanz" ["Influence of the Flow of Material on the Sheet Characterstics and their Consistency"] in a special edition of the journal "Das Papier," No. 10, Vol. 40.

Figure 2A:
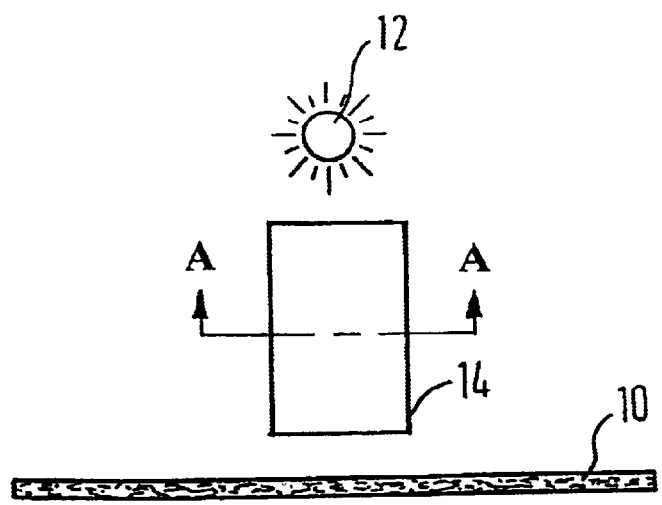
FIG. 2a shows another embodiment of a system for determining fiber orientation which uses a single source side polarizing filter and a single sensor side polarizing filter.
Figure 2A:
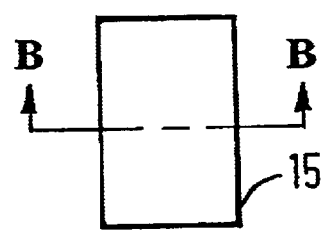
Figure 2A:
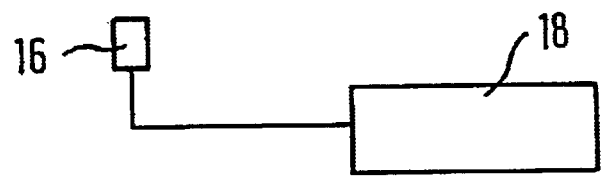
Figure 2B:
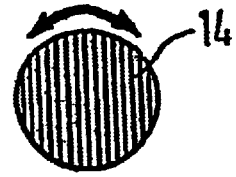
FIG. 2b shows a cross-section A—A view of the source side polarizing filter with polarizing oriented parallel to the web running direction and rotatably mounted.
Figure 2C:
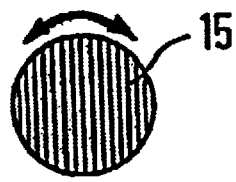
FIG. 2c shows a cross-section B—B view of the sensor side polarizing filter with polarizing oriented parallel to the web running direction and rotatably mounted.

In the embodiment in FIGS. 2a–c, only one polarizing filter 15 is located on the sensor side of paper web 10. Associated with filter 15 is a sensor 16 connected to analysis unit 18. For the purpose of identifying several direction-dependent signals which, in the aforementioned exemplary embodiment of FIGS. 1a–c, are obtained by providing multiple polarizing filters with different orientations, polarizing filter 15 in FIGS. 2a, 2c is mounted such that it can rotate about an axis running perpendicular to paper web 10. Alternatively, filter 14 which is arranged on the source side of paper web 10 can also be rotated. Moreover, both filter 14 and filter 15 can be rotatably mounted. During the measurement in these embodiments, the measured intensity of the light radiation is identified for each angle of rotation of the relevant filter 15 or 14.

Figure 3A:
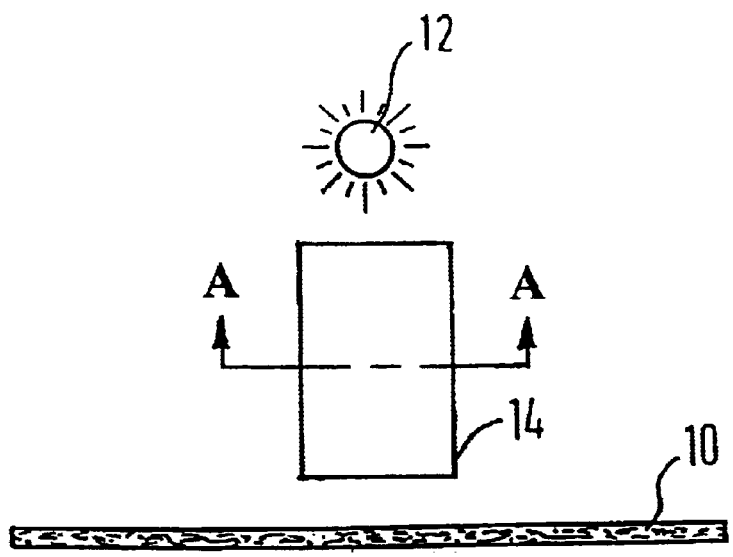
FIG. 3a shows another embodiment of a system for determining fiber orientation which uses a single source side polarizing filter. This embodiment does not require a sensor side polarizing filter.
Figure 3A:
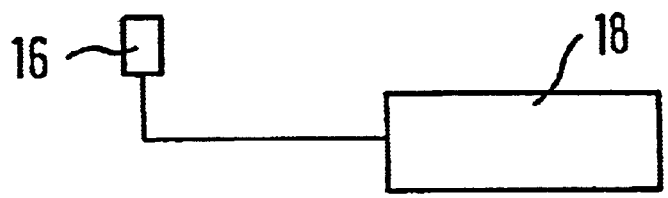
Figure 3B:
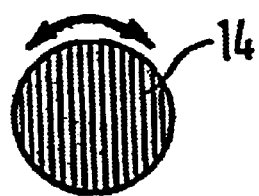
FIG. 3b shows a cross-section A—A view of the source side polarizing filter with polarizing oriented parallel to the web running direction and rotatably mounted.

FIGS. 3a–b show another exemplary embodiment of the invention in which only one optical device in the form of a polarizing filter 14 is provided. Filter 14 is located between light source 12 and paper web 10. The direction-dependent intensity values for this embodiment are obtained sequentially by rotation of filter 14 and by utilizing sensor 16. The fiber orientation is subsequently identified from these values.

Figure 4A:
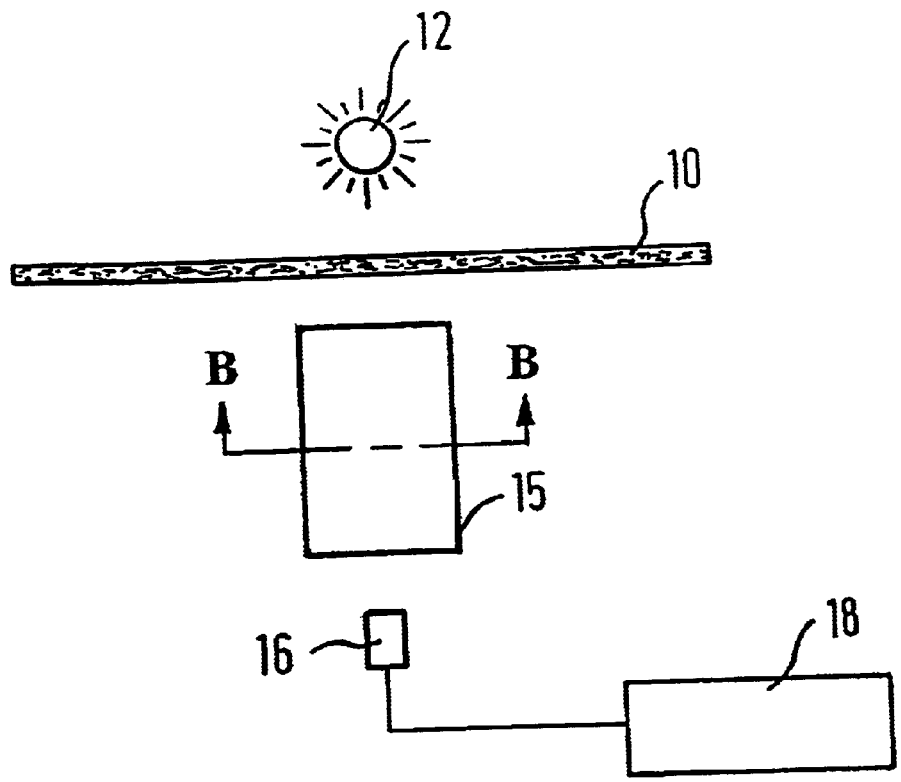
FIG. 4a shows another embodiment of a system for determining fiber orientation which uses a single sensor side polarizing filter. This embodiment does not require a source side polarizing filter.
Figure 4B:
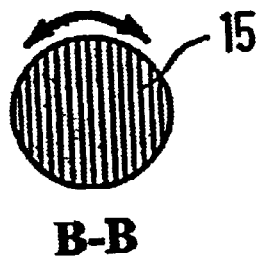
FIG. 4b shows a cross-section A—A view of the sensor side polarizing filter with polarizing oriented parallel to the web running direction and rotatably mounted.

In another exemplary embodiment shown in FIGS. 4a–b, again only one polarizing filter 15 is provided. Filter 15 is located between paper web 10 and sensor 16. Moreover, filter 15 is rotatably mounted in order to obtain a multiplicity of direction-dependent measured values.

In similar fashion to the exemplary embodiment described with respect to FIGS. 1a–c, it is also possible to utilize measured values obtained in each case with two different orientations to form a difference signal, a ratio signal, and a summation signal in the variants using rotating polarizing filters 14 or 15 as per FIGS. 2a–c, 3a–b and 4a–b.

In all embodiments of the invention explained above, the measurement is preferably performed simultaneously with several different wavelengths, working with a light or radiation source 12 emitting a wavelength spectrum and utilizing sensors 16 designed as spectrometers.

Moreover, the signals supplied by sensors 16 are preferably subjected to a data reduction process in analysis unit 18, preferably using a PLS process (Partial Least Squares process).

Furthermore, additional optical devices could be provided in each case, which serve such purposes as performing simultaneous measurements with reference radiation.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects.

Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE CHARACTERS 10 fibrous material web, paper web
12 radiation source, light source
14, 15 optical devices, polarizing filters
16 sensors
18 analysis unit

What is claimed is:

1. A system for determining the orientation and/or distribution of fibers in a fibrous material web, the system comprising:
   at least one source of electromagnetic radiation disposed on one side of the fibrous material web;
   at least one sensor for sensing the electromagnetic radiation emitted by the at least one source disposed on another side of the fibrous material web;
   at least one optical device disposed between the at least one source and the at least one sensor; and
   an analysis unit which analyzes signals from the at least one sensor to identify the fiber orientation and/or distribution of the fibrous material web,
   wherein the electromagnetic radiation travels through the at least one optical device and the fibrous material web such that the at least one optical device influences a propagation of the electromagnetic radiation as a function of its polarization properties.

2. The system of claim 1, wherein the fibrous material web is a paper web.

3. The system of claim 1, wherein the at least one optical device provides for the transmission of linearly polarized radiation.

4. The system of claim 1, wherein the at least one optical device is a polarizing filter.

5. The system of claim 1, wherein the at least one optical device comprises at least two optical devices, one optical device being disposed on one side of the fibrous material web and another optical device being disposed on another side of the fibrous material web.

6. The system of claim 1, wherein the at least one optical device comprises a single optical device disposed between the at least one sensor and the fibrous material web.

7. The system of claim 6, wherein the electromagnetic radiation emitted by the at least one source is polarized before it passes through the fibrous material web.

8. The system of claim 1, wherein the at least one optical device comprises a single optical device disposed between the at least one source and the fibrous material web.

9. The system of claim 1, wherein the electromagnetic radiation comprises one of a discrete and a continuous wavelength spectrum.

10. The system of claim 1, wherein the electromagnetic radiation comprises a discrete and a continuous wavelength spectrum.

11. The system of claim 1, wherein the electromagnetic radiation comprises one of visible light and infrared radiation.

12. The system of claim 1, wherein the electromagnetic radiation comprises visible light and infrared radiation.

13. The system of claim 1, wherein the at least one sensor comprises one of a spectrometer and a photodiode.

14. A system for determining the orientation of fibers in a fibrous material web, the system comprising:
  at least one source of electromagnetic radiation disposed on one side of the fibrous material web;
  at least one sensor for sensing the electromagnetic radiation emitted by the at least one source disposed on another side of the fibrous material web; and
  at least one optical device disposed between the at least one source and the at least one sensor,
  wherein the electromagnetic radiation travels through the at least one optical device and the fibrous material web such that the at least one optical device influences a propagation of the electromagnetic radiation as a function of its polarization properties,
  wherein the at least one optical device provides for the transmission of linearly polarized radiation and
  wherein the at least one optical device is rotatably mounted about an axis.

15. The system of claim 14, wherein the axis is approximately perpendicular to a running direction of the fibrous material web.

16. A system for determining the orientation of fibers in a fibrous material web, the system comprising:
  at least one source of electromagnetic radiation disposed on one side of the fibrous material web;
  at least one sensor for sensing the electromagnetic radiation emitted by the at least one source disposed on another side of the fibrous material web; and
  at least one optical device disposed between the at least one source and the at least one sensor,
  wherein the electromagnetic radiation travels through the at least one optical device and the fibrous material web such that the at least one optical device influences a propagation of the electromagnetic radiation as a function of its polarization properties, and
  wherein the at least one optical device comprises at least two optical devices, the at least two optical devices being disposed on one side of the fibrous material web.

17. The system of claim 16, wherein the at least two optical devices are disposed between the at least one sensor and the fibrous material web.

18. The system of claim 17, wherein each of the at least two optical devices have a different orientation relative to a running direction of the fibrous material web.

19. The system of claim 16, further comprising an additional optical device disposed between the at least one source and the fibrous material web.

20. The system of claim 19, wherein the at least two optical devices are oriented symmetrically relative to the additional optical device.

21. The system of claim 16, wherein each of the at least two optical devices is rotatably mounted about an axis.

22. The system of claim 21, wherein each of the at least two optical devices is rotatable in opposite directions from one another.

23. The system of claim 17, wherein the at least one sensor comprises at least two sensors, each of the sensors being associated with an optical device.

24. A system for determining the orientation of fibers in a fibrous material web, the system comprising:
  at least one source of electromagnetic radiation disposed on one side of the fibrous material web;
  at least one sensor for sensing the electromagnetic radiation emitted by the at least one source disposed on another side of the fibrous material web; and
  at least one optical device disposed between the at least one source and the at least one sensor,
  wherein the electromagnetic radiation travels through the at least one optical device and the fibrous material web such that the at least one optical device influences a propagation of the electromagnetic radiation as a function of its polarization properties,
  wherein the at least one optical device comprises a single optical device disposed between the at least one sensor and the fibrous material web, and
  wherein the single optical device is rotatably mounted.

25. A system for determining the orientation of fibers in a fibrous material web, the system comprising:
  at least one source of electromagnetic radiation disposed on one side of the fibrous material web;
  at least one sensor for sensing the electromagnetic radiation emitted by the at least one source disposed on another side of the fibrous material web; and
  at least one optical device disposed between the at least one source and the at least one sensor,
  wherein the electromagnetic radiation travels through the at least one optical device and the fibrous material web such that the at least one optical device influences a propagation of the electromagnetic radiation as a function of its polarization properties,
  wherein the at least one optical device comprises a single optical device disposed between the at least one source and the fibrous material web, and
  wherein the electromagnetic radiation sensed by the at least one sensor passes through the fibrous material web without being polarized.

26. A system for determining the orientation of fibers in a fibrous material web, the system comprising:
  at least one source of electromagnetic radiation disposed on one side of the fibrous material web;
  at least one sensor for sensing the electromagnetic radiation emitted by the at least one source disposed on another side of the fibrous material web; and
  at least one optical device disposed between the at least one source and the at least one sensor,
  wherein the electromagnetic radiation travels through the at least one optical device and the fibrous material web such that the at least one optical device influences a propagation of the electromagnetic radiation as a function of its polarization properties,
  wherein the at least one optical device comprises a single optical device disposed between the at least one source and the fibrous material web, and
  wherein the single optical device is rotatably mounted.

27. A method for determining the orientation and/or distribution of fibers in a fibrous material web, the method comprising:
  exposing a first side of the fibrous material web to electromagnetic radiation from at least one source;
  allowing the electromagnetic radiation to penetrate to a second side of the fibrous material web;
  influencing a propagation of the electromagnetic radiation as a function of its polarization properties with at least one optical device disposed between the at least one source and at least one sensor;
  sensing the electromagnetic radiation on the second side with the at least one sensor; and
  analyzing with an analysis unit signals from the at least one sensor to identify the fiber orientation and/or distribution of the fibrous material web.

28. The method of claim 27, wherein the fibrous material web is a paper web.

29. The method of claim 27, wherein the at least optical device comprises a polarizing filter disposed between the at least one source and the at least one sensor.

30. The method of claim 27, wherein the influencing further comprises disposing a first optical device on the first side and a second optical device on the second side.

31. The method of claim 30, wherein the influencing further comprises continuously moving the fibrous material web between the first optical device and the second optical device.

32. The method of claim 27, wherein the influencing further comprises continuously moving the fibrous material wed between the at least one source and the at least one sensor.

33. The method of claim 27, wherein the analyzing occurs after the sensing.

34. The method of claim 27, wherein the exposing comprises using a plurality of different sources.

35. The method of claim 34, wherein the different sources vary a wavelength of the electromagnetic radiation over time.

36. The method of claim 27, wherein the analyzing comprises determining at least one of a difference signal, a summation signal and a ratio signal.

37. The method of claim 27, wherein the analyzing comprises analyzing signals generated by a plurality of sensors using the analysis unit which is coupled to the plurality and determining at least one of a difference signal, a summation signal and a ratio signal.

38. The method of claim 37, wherein the determining comprises determining a difference signal, a summation signal and a ratio signal.

39. The method of claim 27, further comprising moving the fibrous material web between the at least one source and the at least one sensor.

40. The method of claim 39, wherein the moving is at a constant speed.

41. The method of claim 40, wherein the fibrous material web is a paper web.

42. The method of claim 27, wherein the electromagnetic radiation comprises one of a visible light and a infrared radiation.

43. The method of claim 42, wherein the influencing comprises first polarizing the electromagnetic radiation on the first side using a first polarizing filter and then polarizing the electromagnetic radiation on the second side using a second polarizing filter.

44. A method for determining the orientation of fibers in a fibrous material web, the method comprising:
exposing a first side of the fibrous material web to electromagnetic radiation from at least one source;
allowing the electromagnetic radiation to penetrate to a second side of the fibrous material web;
influencing a propagation of the electromagnetic radiation as a function of its polarization properties with at least one optical device disposed between the at least one source and at least one sensor; and
sensing the electromagnetic radiation on the second side with the at least one sensor,
wherein the influencing further comprises disposing a first optical device on the first side and a second optical device on the second side, and
wherein the influencing further comprises rotating the first optical device about an axis.

45. The method of claim 44, wherein the second optical device comprises a plurality of optical devices.

46. The method of claim 45, wherein the plurality of optical devices are arranged adjacent one another, each of the plurality being oriented to influence the propagation differently.

47. A method for determining the orientation of fibers in a fibrous material web, the method comprising:
exposing a first side of the fibrous material web to electromagnetic radiation from at least one source;
allowing the electromagnetic radiation to penetrate to a second side of the fibrous material web;
influencing a propagation of the electromagnetic radiation as a function of its polarization properties with at least one optical device disposed between the at least one source and at least one sensor; and
sensing the electromagnetic radiation on the second side with the at least one sensor,
wherein the influencing further comprises disposing a first optical device on the first side and a second optical device on the second side, and
wherein the influencing further comprises rotating the second optical device about an axis.

48. A method for determining the orientation of fibers in a fibrous material web, the method comprising:
exposing a first side of the fibrous material web to electromagnetic radiation from at least one source;
allowing the electromagnetic radiation to penetrate to a second side of the fibrous material web;
influencing a propagation of the electromagnetic radiation as a function of its polarization properties with at least one optical device disposed between the at least one source and at least one sensor;
sensing the electromagnetic radiation on the second side with the at least one sensor; and
analyzing the electromagnetic radiation after the sensing,
wherein the analyzing further comprises analyzing the electromagnetic radiation separately by wavelength.

49. A method for determining the orientation of fibers in a fibrous material web, the method comprising:
exposing a first side of the fibrous material web to electromagnetic radiation from at least one source;
allowing the electromagnetic radiation to penetrate to a second side of the fibrous material web;
influencing a propagation of the electromagnetic radiation as a function of its polarization properties with at least one optical device disposed between the at least one source and at least one sensor; and
sensing the electromagnetic radiation on the second side with the at least one sensor,
wherein the exposing comprises varying a wavelength of the electromagnetic radiation over time.

50. A method for determining the orientation of fibers in a fibrous material web, the method comprising:
exposing a first side of the fibrous material web to electromagnetic radiation from at least one source;
allowing the electromagnetic radiation to penetrate to a second side of the fibrous material web;
influencing a propagation of the electromagnetic radiation as a function of its polarization properties with at least one optical device disposed between the at least one source and at least one sensor; and
sensing the electromagnetic radiation on the second side with the at least one sensor, wherein the electromagnetic radiation comprises one of a visible light and an infrared radiation, wherein the influencing comprises first polarizing the electromagnetic radiation on the first side using a first polarizing filter and then polarizing the electromagnetic radiation on the second side using a second polarizing filter, and wherein one of the first polarizing filter and the second polarizing filter is rotatable.

51. A method for determining the orientation of fibers in a fibrous material web, the method comprising:

exposing a first side of the fibrous material web to electromagnetic radiation from at least one source;

allowing the electromagnetic radiation to penetrate to a second side of the fibrous material web;

influencing a propagation of the electromagnetic radiation as a function of its polarization properties with at least one optical device disposed between the at least one source and at least one sensor; and sensing the electromagnetic radiation on the second side with the at least one sensor, wherein the electromagnetic radiation comprises one of a visible light and an infrared radiation, wherein the influencing comprises first polarizing the electromagnetic radiation on the first side using a first polarizing filter and then polarizing the electromagnetic radiation on the second side using a second polarizing filter, and wherein the polarizing on the first side comprises using a rotatable first polarizing filter.

52. A method for determining the orientation of fibers in a fibrous material web, the method comprising:

exposing a first side of the fibrous material web to electromagnetic radiation from at least one source;

allowing the electromagnetic radiation to penetrate to a second side of the fibrous material web;

influencing a propagation of the electromagnetic radiation as a function of its polarization properties with at least one optical device disposed between the at least one source and at least one sensor; and sensing the electromagnetic radiation on the second side with the at least one sensor, wherein the electromagnetic radiation comprises one of a visible light and an infrared radiation, wherein the influencing comprises first polarizing the electromagnetic radiation on the first side using a first polarizing filter and then polarizing the electromagnetic radiation on the second side using a second polarizing filter, and wherein the polarizing on the second side comprises using a plurality of oriented second polarizing filters.

53. The method of claim 52, wherein each of the plurality of second polarizing filters are rotatable.

54. A system for determining the orientation and/or distribution of fibers in a fibrous material web, the system comprising:

at least one source of electromagnetic radiation disposed on one side of the fibrous material web;

at least one sensor for sensing the electromagnetic radiation emitted by the at least one source disposed on another side of the fibrous material web;

at least one polarizing filter disposed between the at least one source and the at least one sensor; and an analysis unit which analyzes signals from the at least one sensor to identify the fiber orientation and/or distribution of the fibrous material web, wherein the electromagnetic radiation travels through the at least one polarizing filter and the fibrous material web such that the at least one polarizing filter influences a propagation of the electromagnetic radiation as a function of its polarization properties.

55. A method for determining the orientation and/or distribution of fibers in a fibrous material web, the method comprising:

exposing a first side of the fibrous material web to electromagnetic radiation from at least one source;

allowing the electromagnetic radiation to penetrate to a second side of the fibrous material web;

influencing a propagation of the electromagnetic radiation as a function of its polarization properties with at least one polarizing filter disposed between the at least one source and at least one sensor;

sensing the electromagnetic radiation on the second side with the at least one sensor; and analyzing with an analysis unit signals from the at least one sensor to identify fiber orientation and/or distribution of the fibrous material web.

* * * * *